United States Patent [19]

Wieland

[11] Patent Number: 5,103,002

[45] Date of Patent: Apr. 7, 1992

[54] CERAMIDE DERIVATIVES AND THEIR USE AS INHIBITORS OF SPHINGOLIPID SYNTHESIS

[76] Inventor: Felix Wieland, Bergstrasse 80, 6900 Heidelberg, Fed. Rep. of Germany

[21] Appl. No.: 525,391

[22] Filed: May 17, 1990

[30] Foreign Application Priority Data

May 17, 1989 [DE] Fed. Rep. of Germany ....... 3916072

[51] Int. Cl.$^5$ ............... C07D 295/108; C07D 295/13; C07D 233/20
[52] U.S. Cl. .................................. 544/168; 564/224; 568/415; 560/129
[58] Field of Search ........................ 564/224; 544/168; 560/129; 568/415

[56] References Cited

PUBLICATIONS

Journal of Theoretical Biology; Conformation of N-Formyl-1,3-Dihydroxy-$\Delta^{31}$-Penlene, A Model Compound of Sphrgomylin, Kang et al. (1976) 63, 117-124.

Patent Abstracts of Japan JP-A-60190745, Kenkyosho 2/86.

Primary Examiner—Mary C. Lee
Assistant Examiner—Peter Davis
Attorney, Agent, or Firm—Robert W. Becker & Associates

[57] ABSTRACT

Ceramide derivatives of the following general formula

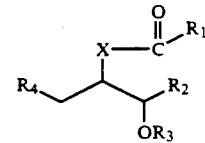

are described, wherein the individual radicals have the following meanings:
X = —NH or —CH$_2$,
R$_1$ = H or C$_{1-11}$-alkyl,
R$_2$ = C$_{2-9}$-alkenyl, wherein the double bond is in α position to the OR$_3$ group
R$_3$ = H, C$_{1-6}$-alkyl or C$_{1-6}$-acyl and
R$_4$ = OH, C$_{1-6}$-alkoxy or morpholino.

These ceramide derivatives represent inhibitors of the biosynthesis of sphingolipids.

6 Claims, No Drawings

CERAMIDE DERIVATIVES AND THEIR USE AS INHIBITORS OF SPHINGOLIPID SYNTHESIS

BACKGROUND OF THE INVENTION

The invention relates to ceramide derivatives and their use as inhibitors of sphingolipid synthesis.

Sphingolipids are understood to be lipids in which instead of the diacetyl glycerol present in the phospholipids an aminodialcohol, i.e. the sphingosine of the following formula

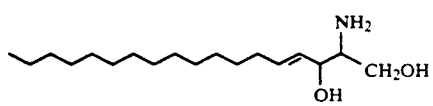

is contained.

The naturally occurring sphingolipids include the so-called ceramides in which a fatty acid radical is present at the amino group. "Ceramide" itself is the term generally used for N-palmityl sphingosine of the following formula:

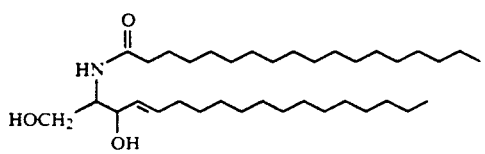

Like other sphingolipids, ceramides perform important functions in the buildup of cell membranes. The investigation of cell membranes and their transport mechanisms represents a biochemical research area of general interest. From the medical side as well there is great interest in such transport mechanisms because numerous metabolic diseases exist which are related to a disturbance of the sphingolipid metabolism, generally involving an increase in the concentration of specific sphingolipids in the body.

The problem underlying the invention is to prepare inhibitors of sphingolipid synthesis in mammal cells with which specific investigations of metabolic and transport mechanisms of sphingolipids can be carried out.

It has been found according to the invention that ceramides having carbon chains which are shortened both in the sphingosine part and in the fatty acid part surprisingly exhibit an inhibitory action on sphingolipid synthesis in mammal cells.

SUMMARY OF THE INVENTION

The subject of the invention is ceramide derivatives of the general formula

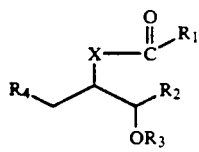

wherein the individual radicals have the following meanings:
X=NH or CH$_2$,
R$_1$=H or C$_{1-11}$-alkyl,
R$_2$=C$_{2-9}$-alkenyl, wherein the double bond is in α position to the C-atom carrying the OR$_3$ group
R$_3$=H, C$_{1-6}$-alkyl or C$_{1-6}$-acyl and
R$_4$=OH, C$_{1-6}$-alkoxy or morpholino In a preferred group of compounds of the invention the individual radicals have the following meanings:
X=NH,
R$_1$=C$_{1-8}$-alkyl
R$_2$=C$_{3-6}$-alkenyl
R$_3$=H, methyl or acetyl and
R$_4$=OH, OCH$_3$ or morpholino The double bond of the alkenyl radical is preferably in α-position to the C-atom carrying the OR$_3$ group and preferably has the trans-configuration, although the cis-compounds are also of particular interest, as will be explained hereinafter.

A particularly preferred compound of the invention is (2S, 3R, 4E)-2-octanoylamino-4-octene-1,3-diol (hereinafter referred to as compound 6) of the following formula:

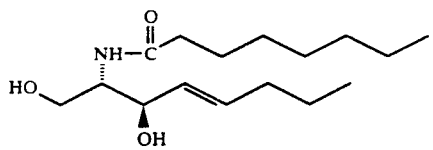

A further preferred compound is the compound of the formula:

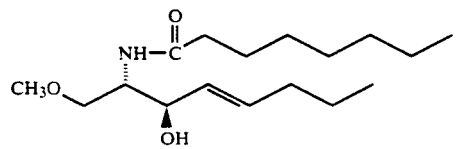

A further preferred compound is (2S,3R, 4E)-2-decenoyl-amino-4-decen-1-morpholino-3-ol of the following formula

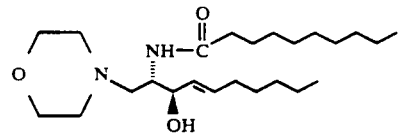

Furthermore, the invention relates to the use of ceramide derivatives of the general formula

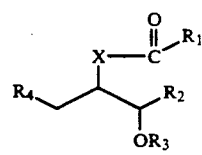

wherein the individual radicals have the following meanings:
X= —NH or —CH$_2$,
R$_1$=H or C$_{1-11}$-alkyl,
R$_2$=C$_{2-9}$-alkyl or C$_{2-9}$-alkenyl,
R$_3$=H, C$_{1-6}$-alkyl or C$_{1-6}$-acyl and
R$_4$=OH, C$_{1-6}$-alkoxy or morpholino
as inhibitors of sphingolipid synthesis.

Although the mechanism of the inhibitory action of the compounds of the invention is not known, the following speculative explanation is conceivably correct. If shortened ceramide is added to a cell culture medium, due to its amphilphilic properties said compound can diffuse practically unrestricted through the plasma membrane of the cells into the cytosol or cytoplasm and from there through the organelle membranes into the interior of cell compartments or organelles. There, for example in Golgi's apparatus or Golgi's complex, they can serve as substrate for the synthesis of shortened sphingolipids, for example cerebrosides and sphingomyelins. Now, due to their polar head group these shortened sphingolipids can no longer freely permeate through membranes but (probably via the path of biosynthetic transport of endogenic sphingolipids) are transported to the plasma membrane. In contrast to the normal sphingolipids, due to their shortened hydrophobic tails the short sphingolipids do not however remain anchored in the plasma membrane but are given up to the surrounding medium (or blood). In this manner the synthesis of endogenic physiological lipids is suppressed.

The cis-compounds are of interest because as far as is known they are not glycosylated but are no doubt converted to sphingomyelin. This represents an interesting specifity.

The present compound with the methyl group as $R_4$ is of particular interest as potential inhibitor of glycosphingolipid synthesis.

The preparation of the shortened ceramides according to the invention is carried out analogously to the recently described synthesis of naturally occurring ceramides. This known synthesis runs via a 2,4-di-O-protected D-threose easily accessible from D-galactose and representing an intermediate product for D-erythrosphingosine synthesis, said synthesis taking place via a trans-selective Witting reaction, introduction of an azide group at the unprotected hydroxyl group and subsequent azide reduction (cf. Richard R. Schmidt and P. Zimmermann, Tetrahedron Letters, Vol. 27 (1986), p.481–484).

DESCRIPTION OF PREFERRED EMBODIMENTS

Hereinafter the invention will be explained in detail with the aid of examples. Example 1 describes with the aid of the following reaction scheme the preparation of compounds numbers 6 and 7 according to the invention whilst in example 2 the results of biochemical investigations using compound number 6 are given.

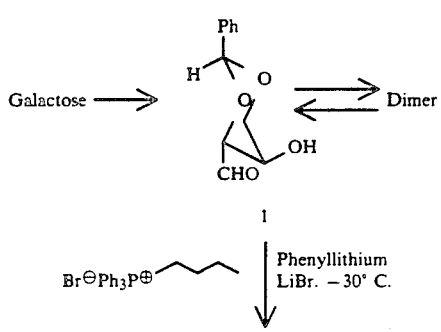

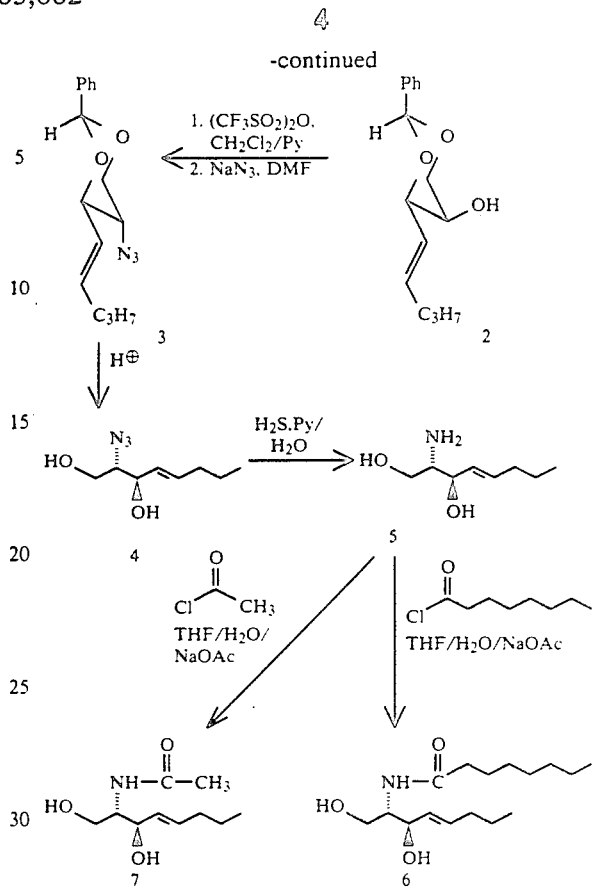

EXAMPLE 1

General particulars regarding the methods and materials:

The solvents used are purified by usual methods. $^1$H-NMR-spectra: Bruker WM250 Cryospec and Jeol JNM-GX400. Tetramethyl silane as inner standard—column chromatography: silica gel 60 (Merck; grain size 0.063–0.2 mm). —Flash chromatography: silica gel 60 (Merck; grain size 0.040–0.063 mm), —medium-pressure chromatography; LiChroprep Si 60 (Merck; grain size 15–25 μm). —Thin-film chromatography: DC plastic films, silica gel 60 $F_{254}$ (Merck; film thickness 0.2 mm). —Melting points were determined in the copper block; they are not corrected. Amounts of rotation: Perkin-Elmer 241 MC; 1-dm-cell.

2,4-O-benzylidene-D-threose (1) *

30.0 g (111 mMol) 4,6-O-benzylidene-D-galactose** are reacted in about 1.2 liter phosphate buffer with pH 7.6 with 50.0 g (257 mMol) sodium periodate.

* P. Zimmermann and R. R. Schmidt, Lieb,Ann.Chem., (1988), p.663–667; ** E. G. Gros and V. Deulofeu, J.Org.Chem., Vol. 29 (1964), p. 3647–3654.

Yield 20.0 g (85%), DC (silica gel; toluene/ethanol, 3:1) $R_f=0.64$.

(2R,3R,4E)-1,3-O-benzylidene-4-octene-1,2,3-triol (2)

52.0 g (130 mMol) butyltriphenyl phosphonium bromide are suspended under nitrogen in 600 ml anhydrous nitrogen-saturated toluene. Phenyl lithium which has been prepared from 6.5 g (940 mMol) lithium and 74 g (470 mMol) bromobenzene in 200 ml anhydrous diethylether is added dropwise without further purification. At the same time the mixture is cooled to −30° C.

Thereafter 21.6 g (104 mMol) (1) in 150 ml anhydrous THF is added dropwise under protective gas conditions. Mixing is then carried out with 150 ml methanol and 250 ml water. The organic phase is prepared by the usual methods. Yield 11.6 g (45%), melting point 42°–43° C., DC (silica gel: petrol ether/acetic ester, 9:1) $R_f=0.16$. $[\alpha]_D^{20}=6.5$ (C=1.00, CHCl$_3$).

$^1$H-NMR (250 MHz, CDCl$_3$): δ=7.54–7.31 (2 m, 5H, C$_6$H$_5$), 5.86 (dt, 1H, CH=CH-CH$_2$, J=6.6 Hz, J=15.6 Hz), 5.65 (dd, 1H, CH=CH—CH$_2$, J=6.1 Hz. J=17 Hz), 5.61 (s, 1H. CH—Ph), 4.39 (d, 1H, O—CH-CH=, J=6.1 Hz), 4.22 (dd, 1H, O—CH$_2$, J=1.8 Hz, J=12 Hz), 4.06 (ddq, 1H, O—CH$_2$, J=12 Hz), 3.52 (dd, 1H, CH-OH, J=1.2 Hz, J=10.4 Hz), 2.71 (d, 1H, OH, J=10.4 Hz), 2.04 (m, 2H, CH=CH—CH$_2$), 1.43 (sext., 2H, CH$_2$—CH$_3$, J=7.3 Hz), 0.91 (t, 3H, CH$_3$, J=7.3 Hz).

(2S,3R,4E)-2-azido-1,3-O-benzylidene-4-octene-1,3-diol (3)

11.0 g (44 mMol) of compound (2) are dissolved away from moisture in 100 ml dichloromethane and 10 ml pyridine. At −15° C. under argon protective gas 15.5 g (55 mMol) trifluoromethane sulfonic acid anhydride are slowly added dropwise. This is then diluted with 100 ml anhydrous dimethyl formamide and 11.4 g (176 mMol) sodium azide added thereto. After two hours vigorous stirring at room temperature the usual processing is carried out.

Yield 7.2 g (60%) colourless oil, DC (silica gel: petrol ether/acetic ester, 9:1) $R_f=0.68$, $[\alpha]_D^{22}=-21.1$ (c=1.00, CHCl$_3$).

$^1$H-NMR (250 MHz, CDCl$_3$): δ=7.56–7.34 (2 m, 5H, C$_6$H$_5$), 5.95 (dt, 1H, CH=CH—CH$_2$. J=6.8 Hz, J=15.6 Hz), 5.58 (dd, 1H, CH=CH-CH$_2$. J=7.3 Hz, J=15.6 Hz), 5.49 (s, 1H. CH—Ph), 4.34 (dd, 1H, O—CH$_2$. J=5.0 Hz, J=11 Hz), 4.06 (dd, 1H, O—CH—CH=, J=7.9 Hz, J=8.5 Hz), 3.61 (dd, 1H. O—CH$_2$, J=11.4 Hz, J=11.4 Hz), 3.52-3.42 (m, 1H, CH—N$_3$), 2.10 (m, 2H, CH=CH—CH$_2$), 1.48 (sext., 2H, CH$_2$—CH$_3$, J=7.3 Hz), 0.93 (t, 3H, CH$_3$, J=7.3 Hz).

(2S,3R,4E)-2-azido-4-octene-1,3-diol (4)

6.5 g (35 mMol) (3) are dissolved in 100 ml anhydrous methanol and after addition of 200 mg (1.05 mMol) p-toluene sulfonic acid monohydrate stirred for 48 hours at room temperature. This is then neutralized by adding solid NaHCO$_3$ and processed in the usual manner.

Yield 4.08 g (63%) colourless oil, DC (silica gel: dichloromethane/methanol, 95:5) $R_f=0.31$, $[\alpha]_D^{20}=-48.03$ (c=1.00, CHCl$_3$).

$^1$NMR (250 MHz, CDCl$_3$): δ=5.82(dt, 1H, CH=CH-CH$_2$, J=6.7 Hz, J=15.6 Hz), 5.55 (dt, 1H, CH=CH—CH$_2$, J=7.2 Hz, J=15.4 HZ), 4.25 (m, 1H, O—CH), 3.78 (m, 2H, O—CH$_2$), 3.53–3.47 (m, 1H, CH—N$_3$), 2.48 (m, 2H, OH), 2.05 (q, 2H, CH=CH—CH$_2$, J=7.6 Hz), 1.43 (sext., 2H, CH$_2$—CH$_3$, J=7.3 Hz), 0.92 (t, 3H, CH$_3$, J=7.3 Hz).

(2S,3R,4E)-2-amino-4-octene-1.3-diol (5)

1.5 g (8 mMol) of compound 4 is stirred at room temperature for 52 hours in 100 ml of an H$_2$S-saturated mixture of water-pyridine (1:1). The processing is then carried out by the usual methods.

Yield 1.2 g (93%) resinous substance, DC (silica gel: chloroform/methanol, 1:1), $R_f=0.19$, $[\alpha]_D^{20}=+2.8$ (c=10, CHCl$_3$).

$^1$H-NMR (400 MHz, CDCl$_3$): δ=5.73 (dt, 1H, CH=CH—CH$_2$, J=6.7 Hz, J=15.4 Hz), 5.45 (dd, 1H, CH=CH—CH$_2$), J=7.1 Hz, J=15.4 Hz), 4.03 (t, 1H, O—CH, J=6.3 Hz), 3.68-3.64 (m, 2H, O—CH$_2$), 3.17 (breites m, 4H, 2OH, NH$_2$), 2.81-2.77 (m, 1H, OH—NH$_2$), 2.03 (q, 2H, CH—CH$_2$, J=7.3 Hz), 1.40 (sext., 2H, CH$_2$—CH$_3$, J=7.3 Hz), 0.91 (t, 3H, CH$_3$, J=7.5 Hz).

Compound (5) can easily be converted with methanolic HCl quantitatively to the hydrochloride derivative.

(2S,3R,4E)-2-octanoylamino-4-octene-1,3-diol (6)

78.6 mg (0.49 mMol) (5) are reacted in a two-phase system of 12 ml THF and 12 ml 50% aqueous sodium acetate solution with vigorous stirring with 80.3 mg (0.49 mMol) octanoic acid chloride. After a reaction time of 12 hours the usual processing is carried out.

Yield 114 mg (82%), melting point 65°-66° C., DC (silica gel: chloroform/methanol 9:1), $R_f=0.45$.

$^1$H-NMR (250 MHz, CDCl$_3$): δ=6.32 (d, 1H, NH, J=7.0 Hz), 5.78 (dt, 1H, CH=CH—CH$_2$, J=6.7 Hz, J=15.6 Hz), 5.53 (dd, 1H, CH=CH—CH$_2$, J=6.4 Hz, J=15.4 Hz), 4.31 (m, 1H, CH—N), 3.96-3.88 (m, 2H, O—CH$_2$, O—CH), 3.72-3.68 (m, 1H, O—CH$_2$), 3.07 (m, 2H, OH), 2.23 (t, 2H, NH—CO—CH$_2$), 2.05 (q, 2H, CH=CH—CH$_2$, J=7.3 Hz), 1.66-1.61 (m, 2H, NH—CO—CH$_2$—CH$_2$), 1.40 (sext., 2H, CH$_2$—CH$_3$, J=7.3 Hz), 1.19-1.37 (m, 8H, CH$_2$), 0.90 (t, 3H, CH$_3$, J=7.3 Hz), 0.88 (t, 3H, CH$_3$, J=7.3 Hz).

(2S,3R,4E)-2-acetylamino-4-octene-1,3-diol (7)

Compound (7) is prepared analogously to the process described for (6) by using 117.9 mg (0.75 mMol) of compound (5) and 58.1 mg (0.74 mg) acetyl chloride.

Yield 119.1 mg (80%) colorless oil, DC (silica gel: chloroform/methanol, 8:2) $R_f=0.54$.

$^1$H-NMR (400 MHz, CDCl$_3$): δ=6.40 (d, 1H, NH, J=7.0 Hz), 5.78 (dt, 1H, CH=CH—CH$_2$, J=6.8 Hz, J=15.4 Hz), 5.56 (dd, 1H, CH—CH—CH$_2$, J=6.4 Hz, J=15.4 Hz), 4.32 (m, 1H, CH—N), 40.03-3.81 (m, 2H, O—CH$_2$, O—CH), 3.79-3.64 (m, 1H, O—CH$_2$), 3.17-2.97 (m, 2H, OH), 2.08-2.03 (m, 5H, CH=CH—CH$_2$, CO—CH$_3$), 1.41 (sext., 2H, CH$_2$—CH$_3$, J=7.3 Hz), 0.90 (t, 3H, CH$_3$, J=7.3 Hz)

(2S,3R,4E)-2-Decanoylamino-4-decen-1-morpholino-3-ol

This compound is prepared analogously to the process described for compound (6), with the exception that compound (4) is reacted with methanesulfonyl chloride and the compound obtained having a mesyl group in the position 1 is reacted with morpholine to yield the corresponding 1-morpholino compound. The latter compound is converted to the title compound analogously to the above reaction scheme.

EXAMPLE 2

To investigate the biochemical action of the compounds of the invention a cell culture of ovarial cells of the Chinese hamster (Chinese Hamster Ovary (CHO) cells) is mixed in an alpha-medium of the company Seromed (0.2% NaHCO$_3$, without antibiotics, without fetal calf serum or with 7.5% fetal calf serum) with compound no. 6 (3H-marked; 2,3-Di-$^3$H-octanoic acid derivative) in a concentration of 5 micromolar and incubated for 180 minutes at 37° C. Thereafter, after centrifugation both the medium and the cell extract (obtained by extraction of the cells with $CH_3OH/H_2O=1:1$) to a thin-film chromatographical investigation under the following conditions: 25 μm Merck silica gel; solvent butanone/acetone/$H_2O=30:3:5$).

The analysis of the resulting products was by
a) digestion tests with specific degradating enzymes. i.e. sphingomyelinase, β-glucosidase and endo-glycoceramidase (enzymes of the companies Boehringer Mannheim and Genzyme) (FIG. 1) and
b) mass-spectroscopic investigation (fast atom bombardment method).

The results of the digestion tests are represented in the autoradiogram of FIG. 1. The individual traces have the following meanings:
1) 2,3-di-$^3$H-octanoic acid
2) 2,3-di-$^3$H-octanoyl-$C_8$-sphingosine (shortened radioactive ceramide $^3$H-GCA) used
3) Medium of incubation of the CHO-cells for 180 minutes at 37° C. with 100 μCi $^3$H-GCA/ml (=ca. 10 μM). 5 μl of the medium was applied; fluorography for 24 h on Kodak X-Omat film.
4) Specimen as in 3) kept for 20 h at 23° C. (as comparison with digestion with sphingomyelinase)
5) Specimen as in 3) and 4) but incubated for 20 h at 23° C. with sphingomyelinase from human placenta (sigma).

The fast atom bombardment analysis gave the following $M^+-$ or $M+H^+$ peaks ($C_8$ compounds mean here the compounds having 8 C-atoms in the sphingosine part and in the fatty acid radical):

| Compound | Peak | |
|---|---|---|
| $C_8$-ceramide (MW 285) | $M + H^+$ | 286 |
| $C_8$-sphingomyeline (MW 451) | $M^+$ | 451 |
| $C_8$-glucosyl ceramide (MW 447) | $M + H^+$ | 448 |

It was possible to measure the rate of formation and transport of $C_8$-sphingomyeline and $C_8$-glucosyl ceramide (FIG. 2). The test for this purpose was carried out as follows.

2 ml CHO-cells in α-MEM medium without fetal calf serum were mixed with 10 nMol (150 μCi) $^3$H-GCA ($C_8$) and stirred at 37° C. in the cell incubator. At the specified times 100 μl aliquot fractions were removed and centrifuged for 30 sec. at 0° C. and 10000 g. The supernatant medium was pipetted off in each case (referred to in FIGS. 2A and 2B as "media"). The cell deposits were extracted with $CH_3OH/H_2O = 1:1$ (100 μl) and again centrifuged. The media and extracts were chromatographed (5 μl in each case) on silica gel 60 (Merck) in butanone/acetone/$H_2O=30:3:5$. The plates were dried and the radioactive spots were quantitatively determined in a Berthold linear TLC radioanalyzer. The count yield at $^3$H with this method is about 1% with respect to cpm in solution. "Cts" represents the total measured pulses (in this test the measuring time was 5 min per trace).

It is apparent from FIGS. 2A and 2B that in the cell a rapid rise of the synthesized compounds takes place to a plateau value which was maintained for hours in the cell. In the medium the compounds occur only after a delay phase and are then linearly accumulated. These findings concur with the hypothesis presented earlier that the shortened ceramide can permeate into the cell, is converted therein and then transported out of the cell. In this manner a competitive in vivo inhibition of sphingolipid synthesis can be obtained.

EXAMPLE 3

Inhibition of the glucosyl ceramide synthesis by (2S,3R,4E)-2-decanoylamino-4-decen-1-morpholino-3-ol The synthesis of the sphingolipids takes place in the Golgi apparatus.

A. Inhibition in intact Golgi membranes

Golgi membranes (20 μl, 60 μg membrane protein) were incubated in tris buffered brine, pH 7.4, for 45 minutes at 37° C. in the presence of increasing amounts of the inhibitor (0, 5, 10, 25, 100, 250 μM final concentration).

In these runs the activity of the sphingolipid synthesis was measured by simultaneous addition of $^3$H ceramide $C_8H_8$ ((2S,3R,4E)-2-octanoylamino-4-octen-1,3-diol) and quantification of the products sphingomyeline $C_8H_8$ and glucosyl ceramide $C_8C_8$ after thin layer chromatography.

B. Inhibition of intact cells

Chinese Hamster Ovary (CHO) cells in suspension were preincubated with the concentrations of inhibitor indicated for 15 minutes at 37° C. The activity of the sphingolipid synthesis was determined as set forth under A after the indicated times in media and cell extracts (cell extracts=precipitate after centrifuging of the aliquots extracted with 50% aqueous isopropanol volume corresponding to the volume of the aliquot).

The results of the experiments A ans B are shown in FIGS. 3 to 5. FIG. 3 shows that the addition of the inhibitor up to the concentration of 250 μM does not influence the synthesis of sphingomyeline $C_8H_8$ whereas the synthesis of glucosyl ceramide decreases to less than 15%. Therefore, (2S, 3R, 4E)-2-decenoylamino-4-decen-1-morpholino-3-ol is considered to be a specific inhibitor of glycosyl ceramide synthesis.

FIGS. 4 and 5 show that the formation of the sphingomyeline $C_8H_8$ (plain bars) is less inhibited than the formation of glucosyl ceramide (hatched bars). The results in cells are more pronounced than in cell media. The results in intact cells are not as clear as in intact Golgi membranes.

The present invention is, of course, in no way restricted to the specific disclosure of the specification and drawings, but also encompasses any modifications within the scope of the appended claims.

I claim:
1. Ceramide derivatives of the general formula

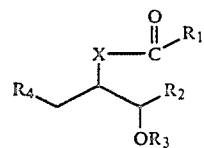

wherein the individual radicals have the following meanings:
$X=$ —NH or —$CH_2$,
$R_1=$H or $C_{1-11}$-alkyl,
$R_2=C_{2-9}$-alkenyl wherein the double bond is in α position to the C-atom carrying the $OR_3$ group, $R_3$ = H, $C_{1-6}$-alkyl or $C_{1-6}$-acyl and
$R_4$ = $C_{1-6}$-alkoxy or morpholino.

2. Compounds according to claim 1, wherein the individual radicals have the following meanings:
X = —NH,
$R_1$ = $C_{1-8}$-alkyl,
$R_2$ = $C_{3-6}$-alkenyl and
$R_3$ = H, methyl or acetyl and
$R_4$ = $OCH_3$ or morpholino.

3. Compounds according to claim 1, wherein the double bond of the alkenyl radical in $R_2$ has the trans-configuration.

4. Compounds according to claim 1, wherein the double bond of the alkenyl radical of $R_2$ has the cis-configuration.

5. Compound according to claim 1 having the following formula:

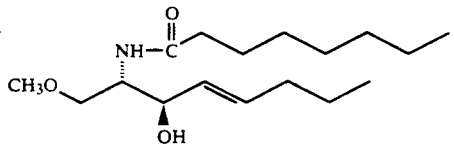

6. Compound according to claim 1 having the following formula

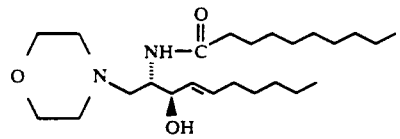

* * * * *